(12) United States Patent
Honda et al.

(10) Patent No.: US 9,155,884 B2
(45) Date of Patent: Oct. 13, 2015

(54) TREATMENT SYSTEM AND ACTUATION METHOD FOR TREATMENT SYSTEM

(71) Applicant: OLYMPUS MEDICAL SYSTEMS CORP., Tokyo (JP)

(72) Inventors: Yoshitaka Honda, Hachioji (JP); Takashi Irisawa, Hachioji (JP); Kazue Tanaka, Sagamihara (JP); Sadayoshi Takami, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 92 days.

(21) Appl. No.: 13/921,333

(22) Filed: Jun. 19, 2013

(65) Prior Publication Data

US 2013/0338740 A1 Dec. 19, 2013

Related U.S. Application Data

(63) Continuation of application No. PCT/JP2012/079369, filed on Nov. 13, 2012.

(60) Provisional application No. 61/569,332, filed on Dec. 12, 2011.

(51) Int. Cl.
*A61B 18/18* (2006.01)
*A61N 1/32* (2006.01)
*A61B 18/08* (2006.01)
*A61B 18/14* (2006.01)
(Continued)

(52) U.S. Cl.
CPC .............. *A61N 1/327* (2013.01); *A61B 18/085* (2013.01); *A61B 18/10* (2013.01); *A61B 18/1442* (2013.01); *A61B 18/1445* (2013.01); *A61B 2018/00678* (2013.01); *A61B 2018/00684* (2013.01); *A61B 2018/00708* (2013.01); *A61B 2018/00779* (2013.01); *A61B 2018/00791* (2013.01); *A61B 2018/00875* (2013.01)

(58) Field of Classification Search
CPC ........... A61B 2018/00589; A61B 2018/00595; A61B 2018/00619; A61B 2018/00678; A61B 2018/00666; A61B 2018/00684; A61B 2018/0063
USPC .................................. 606/31, 38, 42, 50–52
See application file for complete search history.

(56) References Cited

U.S. PATENT DOCUMENTS

2002/0082593 A1 6/2002 Hareyama et al.
2004/0015163 A1* 1/2004 Buysse et al. .................. 606/34
(Continued)

FOREIGN PATENT DOCUMENTS

EP 1 582 165 A1 10/2005
EP 2 106 762 A1 10/2009
(Continued)

*Primary Examiner* — Joseph Stoklosa
*Assistant Examiner* — Jocelyn D Ram
(74) *Attorney, Agent, or Firm* — Scully, Scott, Murphy & Presser, PC

(57) ABSTRACT

A treatment system includes a power source for heat generation which outputs power for heat generation, a grasping member having a heating element which applies the power for heat generation as thermal energy to a grasped living tissue, a storage section storing a power decrease pattern which is a prediction about a change state of the power for heat generation, and a control section which performs pattern control on the power source for heat generation on the basis of the power decrease pattern acquired from the storage section.

16 Claims, 8 Drawing Sheets

(51) Int. Cl.
*A61B 18/10* (2006.01)
*A61B 18/00* (2006.01)

(56) References Cited

U.S. PATENT DOCUMENTS

| | | | |
|---|---|---|---|
| 2004/0092923 A1* | 5/2004 | Miura et al. | 606/28 |
| 2005/0222560 A1* | 10/2005 | Kimura et al. | 606/28 |
| 2008/0015575 A1* | 1/2008 | Odom et al. | 606/51 |
| 2009/0076506 A1* | 3/2009 | Baker | 606/51 |
| 2009/0248002 A1* | 10/2009 | Takashino et al. | 606/28 |
| 2010/0185196 A1* | 7/2010 | Sakao et al. | 606/51 |
| 2011/0077629 A1* | 3/2011 | Tanaka et al. | 606/28 |
| 2012/0191072 A1* | 7/2012 | Hancock | 604/542 |
| 2012/0226272 A1* | 9/2012 | Chernov et al. | 606/34 |
| 2012/0283731 A1* | 11/2012 | Unger et al. | 606/49 |

FOREIGN PATENT DOCUMENTS

| | | |
|---|---|---|
| JP | 2002-238916 A | 8/2002 |
| JP | 2005-218749 A | 8/2005 |
| JP | 2005-253789 A | 9/2005 |
| JP | 2007-159737 A | 6/2007 |
| JP | 2009-247893 A | 10/2009 |
| JP | 2010-538796 A | 12/2010 |
| WO | WO 2009/039179 A1 | 3/2009 |

* cited by examiner

US 9,155,884 B2

TREATMENT SYSTEM AND ACTUATION METHOD FOR TREATMENT SYSTEM

CROSS-REFERENCE TO RELATED APPLICATION

This application is a continuation application of PCT/JP2012/079369 filed on Nov. 13, 2012 and claims benefit of U.S. Provisional Patent Application No. 61/569,332 filed in the U.S.A. on Dec. 12, 2011, the entire contents of which are incorporated herein by this reference.

BACKGROUND OF THE INVENTION

1. Field of the Invention

Embodiments of the present invention relate to a treatment system including one pair of grasping members which apply thermal energy to a grasped living tissue and an actuation method for the treatment system.

2. Description of the Related Art

U.S. Patent Application Publication No. 2009/076506 discloses a treatment system including one pair of grasping members which apply high-frequency power energy and thermal energy to a grasped living tissue, a high-frequency power source which outputs high-frequency power for applying high-frequency power energy, a power source for heat generation which outputs power for heat generation for applying thermal energy, and a control section which controls the high-frequency power source and the power source for heat generation for switching between application of high-frequency power energy and application of thermal energy.

U.S. Patent Application Publication No. 2009/0248002 discloses a treatment system which first applies high-frequency power energy to a living tissue and then starts application of thermal energy. High-frequency power energy acts to release intracellular components including polymer compounds typified by protein by destroying cell membranes in a living tissue and homogenize the intracellular components with extracellular components typified by collagen. Such homogenization of a living tissue promotes joining of a living tissue through subsequent application of thermal energy.

For application of thermal energy, a process is known of raising temperature of a heating element to a predetermined temperature on the basis of a sensed temperature and then performing feedback control so as to hold the temperature at the predetermined temperature.

SUMMARY OF THE INVENTION

A treatment system according to an embodiment includes a power source for heat generation which outputs power for heat generation, a grasping member having a heating element which applies the power for heat generation as thermal energy to a living tissue, a storage section storing a power decrease pattern which is a prediction about a change state of the power for heat generation, and a control section which performs pattern control on the power source for heat generation on the basis of the power decrease pattern acquired from the storage section.

A control method for a treatment system according to another embodiment includes a step in which power for heat generation outputted by a power source for heat generation that is subjected to constant temperature control by a control section is applied as thermal energy to a living tissue by a heating element of the grasping member, a step of acquiring, by the control section, a parameter of power for heat generation on the basis of a change state of the power for heat generation, a step of acquiring, by the control section, a power decrease pattern which is a prediction about a subsequent change state of the power for heat generation from a storage section by using the parameter of power for heat generation, and a step of changing, by the control section, a control method for the power source for heat generation from the constant temperature control to pattern control based on the power decrease pattern.

DETAILED DESCRIPTION OF THE PREFERRED EMBODIMENTS

First Embodiment

<Configuration of Treatment System>

Figure 1:
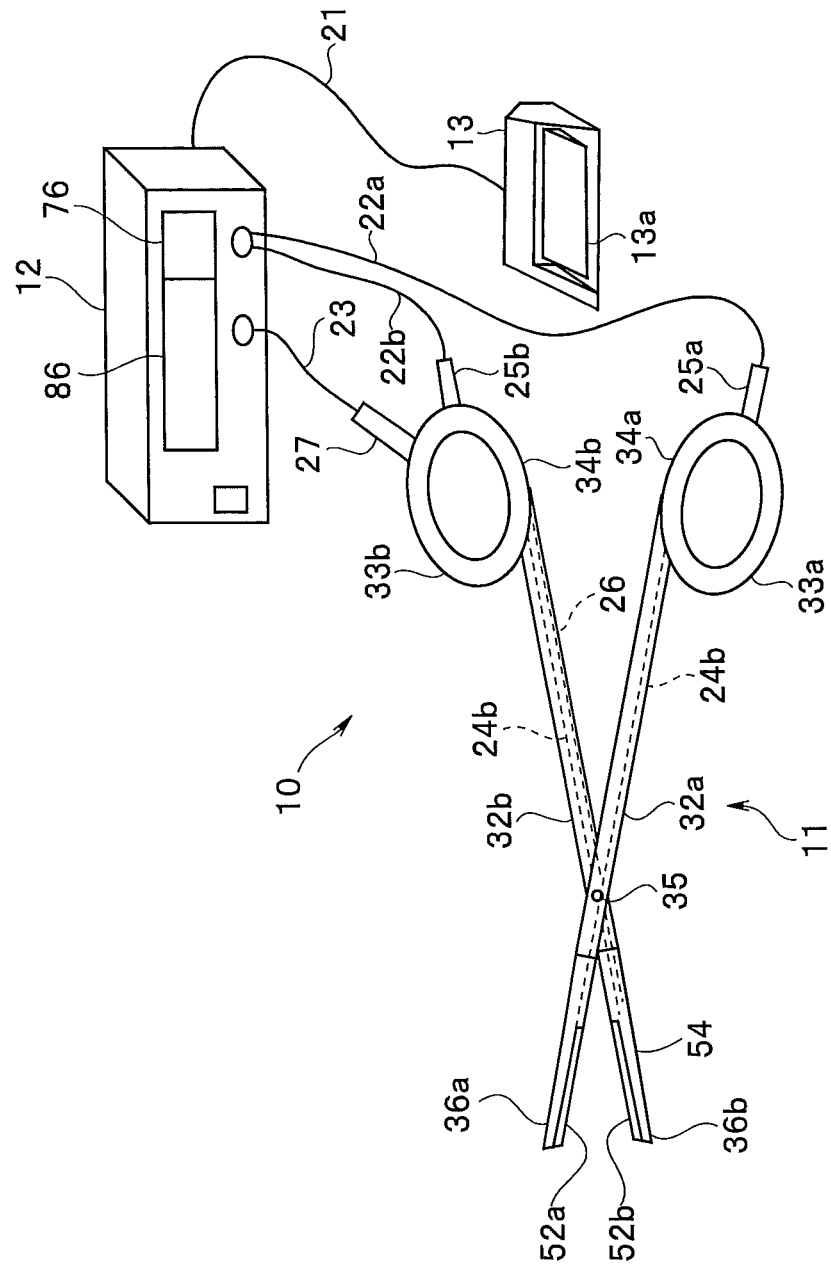
FIG. 1 is an external view of a treatment system according to a first embodiment.

A treatment system 10 according to a first embodiment will first be described. As shown in FIG. 1, the treatment system 10 includes a treatment instrument 11, a power supply portion 12, and a foot switch 13. The treatment system 10 switches between high-frequency power energy and thermal energy and applies, using the power supply portion 12, the energy to a living tissue grasped by jaws 36a and 36b which are one pair of grasping members of the treatment instrument 11. Note that high-frequency power and power for heat generation may hereinafter be abbreviated as "HF" and "TH," respectively. For example, high-frequency power energy is referred to as HF energy.

The treatment instrument 11 is connected to the power supply portion 12 by HF lines 22a and 22b and a TH line 23. Note that although the HF lines 22a and 22b, the TH line 23, and the like each have two pieces of wiring, the two pieces of wiring are expressed as one line. The foot switch 13 is connected to the power supply portion 12 by a switch line 21.

The treatment instrument 11 has one pair of scissors constituent members 32a and 32b, one pair of handle portions 34a and 34b, and the one pair of jaws 36a and 36b. The handle portions 34a and 34b are provided at proximal end portions of the scissors constituent members 32a and 32b. The handle portions 34a and 34b are operated while being held in a hand by a surgeon. The jaws 36a and 36b are provided at distal end portions of the scissors constituent members 32a and 32b to grasp a living tissue to be treated.

The scissors constituent members 32a and 32b are placed one on the other so as to substantially intersect each other between distal ends and proximal ends of the scissors constituent members 32a and 32b. A fulcrum pin 35 which pivotably couples the scissors constituent members 32a and 32b is provided at an intersection portion of the scissors constituent members 32a and 32b.

The handle portions 34a and 34b are provided with rings 33a and 33b on which a surgeon puts his or her fingers. When the surgeon puts a thumb and a middle finger through the rings 33a and 33b, respectively, and opens and closes the rings 33a and 33b, the jaws 36a and 36b open and close in tandem with the motion.

Respective energy release elements which apply energy to a grasped living tissue are disposed at the jaws 36a and 36b. That is, an electrode 52a as the energy release element which has a grasping surface and is made of an electric conductor is disposed at the jaw 36a. An electrode 52b as the energy release element which has a grasping surface and is made of an electric conductor and a heater member 53 as a heating element are disposed at the jaw 36b. The heater member 53 is embedded in the jaw 36b while the heater member 53 is disposed on a reverse surface of the electrode 52b that is made of a high thermal conductor.

Figure 2:
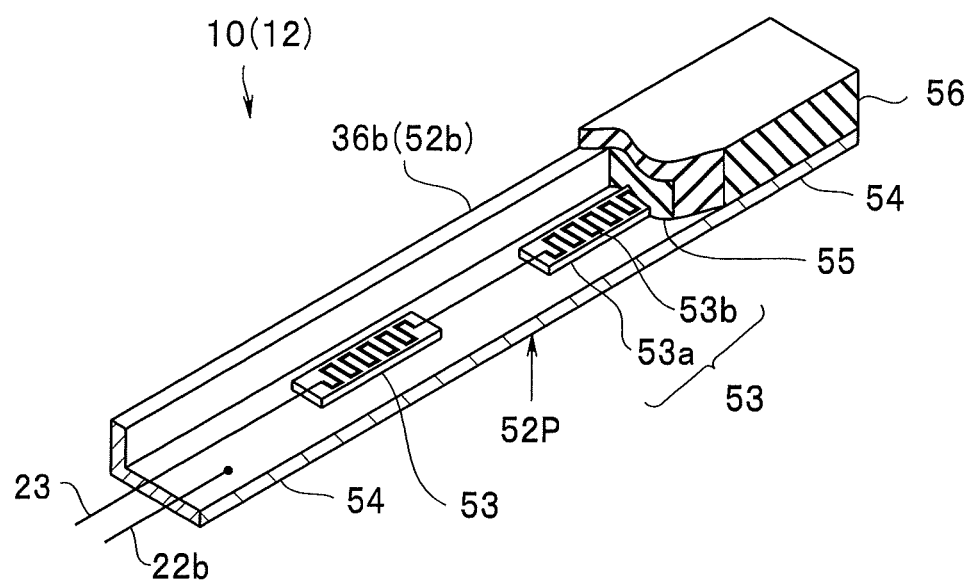
FIG. 2 is a three-dimensional cross-sectional view for explaining a structure of a jaw in the treatment system according to the first embodiment.

That is, as shown in FIG. 2, in the jaw 36b of the treatment instrument 11, the heater member 53 is joined to a surface reverse to a grasping surface 52P of a base 54 which is made of copper. The heater member 53 is covered with a sealing member 55 and a cover member 56. Note that FIG. 2 shows a portion of the jaw 36b and that three or more heater members 53 may be joined to each jaw 36b.

In the heater member 53, a thin-film resistor or a thick-film resistor is disposed as a heating pattern 53b on a substrate 53a of, e.g., alumina or aluminum nitride. The thin-film resistor is made of, e.g., an electrically conductive thin film which is formed by a thin film formation method, such as PVD (physical vapor deposition) or CVD (chemical vapor deposition), or foil of an electrically conductive metal, such as SUS. The thick-film resistor is formed by a thick film formation method, such as screen printing. The heating pattern 53b is formed of a refractory metal material, such as molybdenum, which exhibits a positive temperature coefficient of resistance indicating that electric resistance increases directly with temperature.

Note that the heater member 53 may also be disposed at the jaw 36a of the treatment instrument 11. That is, a heating element only needs to be disposed at at least one grasping member.

HF lines 24a and 24b for supplying HF to the electrodes 52a and 52b are disposed inside the scissors constituent members 32a and 32b, respectively. The HF lines 24a and 24b extend from the jaws 36a and 36b to the handle portions 34a and 34b, respectively. HF terminals 25a and 25b are provided at the rings 33a and 33b, respectively. The HF terminals 25a and 25b are connected to the HF lines 24a and 24b, respectively. For the reason, when HF is supplied to the electrodes 52a and 52b while a living tissue is grasped by the jaws 36a and 36b, HF is passed through the living tissue between the electrodes 52a and 52b. In other words, HF energy is applied to the living tissue.

A TH line 26 for supplying TH to the heater member 53 is disposed inside the scissors constituent member 32b. The TH line 26 extends from the jaw 36b to the handle portion 34b. A TH terminal 27 which is connected to the TH line 26 is provided at the ring 33b. For the reason, when TH is supplied to the heater member 53 through the TH line 26, the heater member 53 generates heat. That is, the TH is converted into thermal energy by the heater member 53, the thermal energy is transferred to the electrode 52b, and the thermal energy is applied to a living tissue in contact with the grasping surface of the electrode 52b.

As described above, when HF is passed between the electrodes 52a and 52b, the treatment instrument 11 applies HF energy to a living tissue grasped between the jaws 36a and 36b. When TH is passed through the heater member 53 in the treatment instrument 11, the TH is converted into the thermal energy. The treatment instrument 11 applies the thermal energy to the living tissue.

The foot switch 13 has a pedal 13a. While the pedal 13a is pressed, the power supply portion 12 outputs HF or TH on the basis of a setting state (a state in which an output value, output timing, and the like are controlled). When the press of the pedal 13a is canceled, the power supply portion 12 forcibly stops outputting the power.

Figure 3:
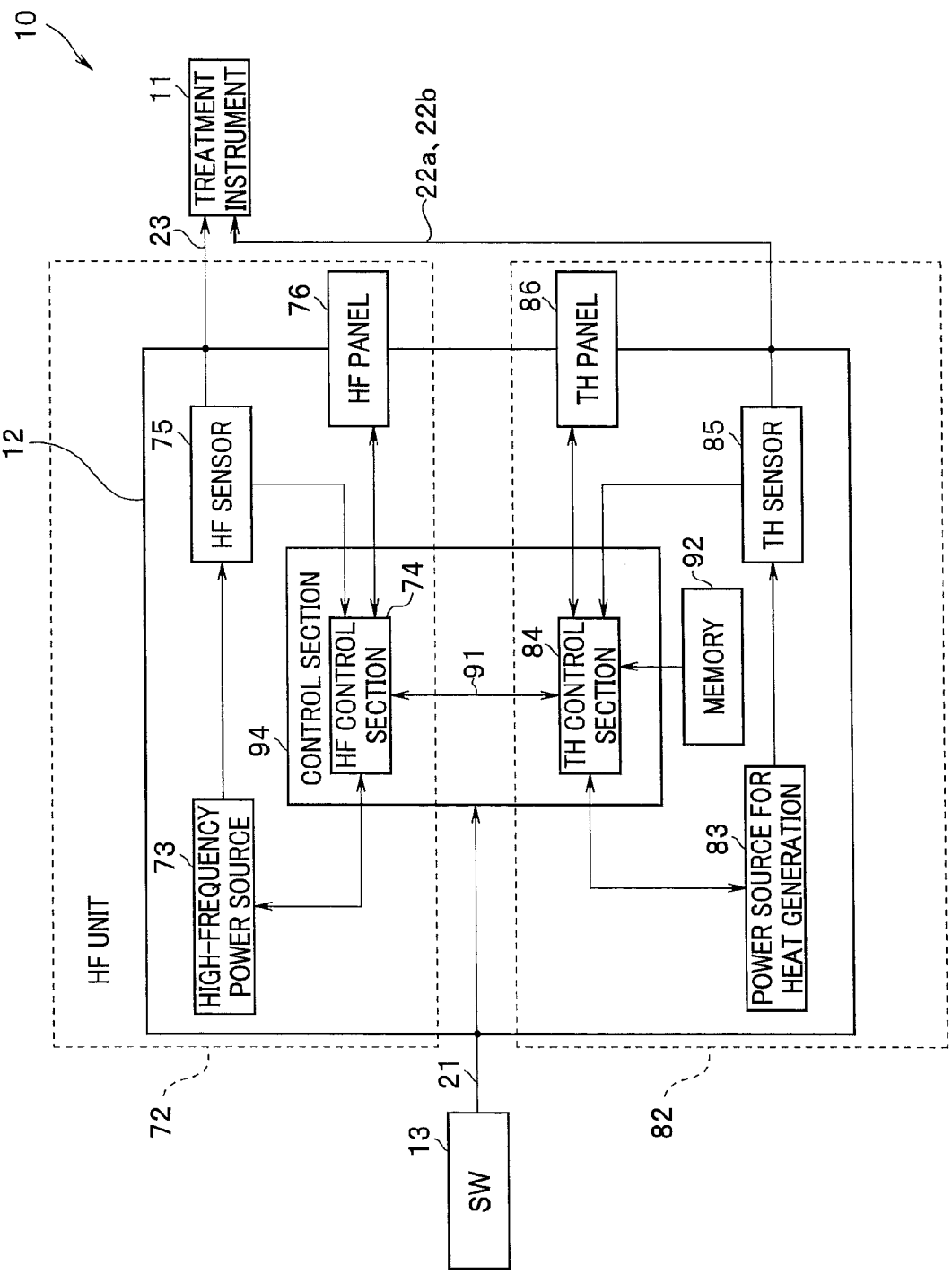
FIG. 3 is a configuration diagram of the treatment system according to the first embodiment.

As shown in FIG. 3, the power supply portion 12 is composed of an HF unit 72 and a TH unit 82. The HF unit 72 has a high-frequency power source 73 which outputs HF, an HF control section 74 which controls the high-frequency power source 73, an HF sensor 75 which is a high-frequency power measuring section which measures voltage and current of HF outputted by the high-frequency power source 73, and an operation panel 76.

The TH unit 82 has a power source 83 for heat generation which outputs TH, a TH control section 84 which controls the power source 83 for heat generation, a TH sensor 85 which is a heat generation power measuring section that measures voltage and current of TH outputted by the power source 83 for heat generation, an operation panel 86, and a memory 92 which is a storage section that is made up of, e.g., a semiconductor memory.

The HF control section 74 and the TH control section 84 are connected by a communication line 91 which can transmit a signal in both directions to constitute a control section 94. That is, the control section 94 that is made up of a computing circuit, such as a CPU, controls the high-frequency power source 73 and the power source 83 for heat generation. The operation panels 76 and 86 each have a setting function portion, with which a surgeon sets a treatment condition, and a display function of displaying a treatment status.

The HF sensor 75 is connected to the treatment instrument 11 via the HF lines 22a and 22b. The high-frequency power source 73 and the HF sensor 75 are connected to the HF control section 74. The HF control section 74 is further connected to the operation panel 76. The HF control section 74 calculates HF information, such as power and impedance, on the basis of information from the HF sensor 75, sends a control signal to the high-frequency power source 73, and sends information to be displayed to the operation panel 76. HF outputted by the high-frequency power source 73 that is controlled by the HF control section 74 is transmitted to the electrodes 52a and 52b of the treatment instrument 11.

The TH control section 84 calculates temperature of the heater member 53 as TH information on the basis of information from the TH sensor 85, in addition to power, a resistance value, and the like. That is, since the heating pattern of the heater member 53 is made of a material having a positive temperature coefficient of resistance, as already described, the TH control section 84 can calculate the temperature of the heater member 53 from a TH resistance value which is calculated from voltage and current of TH. The TH control section 84 sends a control signal to the power source 83 for heat generation on the basis of the TH information. TH outputted by the power source 83 for heat generation that is controlled by the TH control section 84 is transmitted to the heater member 53 of the treatment instrument 11.

Note that the HF control section 74 also sends a control signal to the TH control section 84 at the end of application of HF such that the TH control section 84 starts outputting TH.

As described above, the treatment instrument 11 has a function of a bipolar-type high-frequency treatment instrument and a function of a treatment instrument for heat generation.

Figure 4:
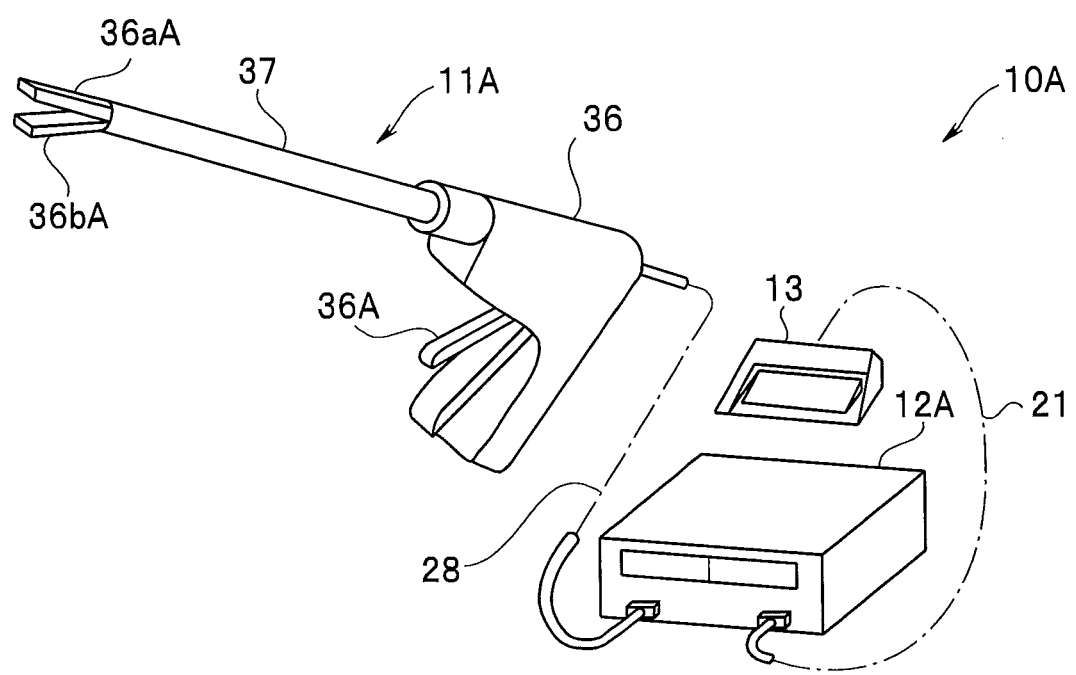
FIG. 4 is an external view of a treatment system according to a modification of the first embodiment.

Note that the treatment instrument of the treatment system according to the embodiment may be a so-called linear-type treatment instrument. For example, a treatment system 10A according to a modification shown in FIG. 4 includes a linear-type treatment instrument 11A, a power supply portion 12A, and the foot switch 13.

The treatment instrument 11A has a handle 36, a shaft 37, and one pair of jaws 36aA and 36bA which are grasping members that grasp a living tissue. Structures of the jaws 36aA and 36bA are identical to the structures of the jaws 36a and 36b.

The handle 36 has a shape which is easy for a surgeon to grip, such as a substantially L-shape. The handle 36 has an open/close knob 36A. The open/close knob 36A is designed such that the jaws 36a and 36b grasp a living tissue when a surgeon presses and operates the open/close knob 36A. HF electrodes (not shown) and heater members (not shown) of the jaws 36aA and 36bA are connected to the power supply portion 12A via a piece 28 of wiring. That is, the piece 28 of wiring is made up of the HF lines 22a and 22b and the TH line 23. A basic configuration and a function of the power supply portion 12A are identical to the basic configuration and the function of the power supply portion 12.

That is, any of treatment instruments having various structures can be used as long as the treatment instrument can apply high-frequency power energy and thermal energy to a grasped living tissue.

<Motion of Treatment System>

An actuation method for the treatment system 10 will be described.

The treatment system 10 first applies HF energy to a grasped living tissue and applies thermal energy after the application of HF energy ends. In other words, the control section 94 controls the high-frequency power source 73 and the power source 83 for heat generation to start applying thermal energy after application of high-frequency power energy ends.

That is, the treatment system 10 switches from HF energy application mode to thermal energy application mode when a process of destroying cell membranes in the living tissue is completed by application of HF energy. In thermal energy application mode, moisture is removed by further raising temperature of the living tissue, and a process of joining the living tissue is performed through hydrogen bonding.

Figure 5:
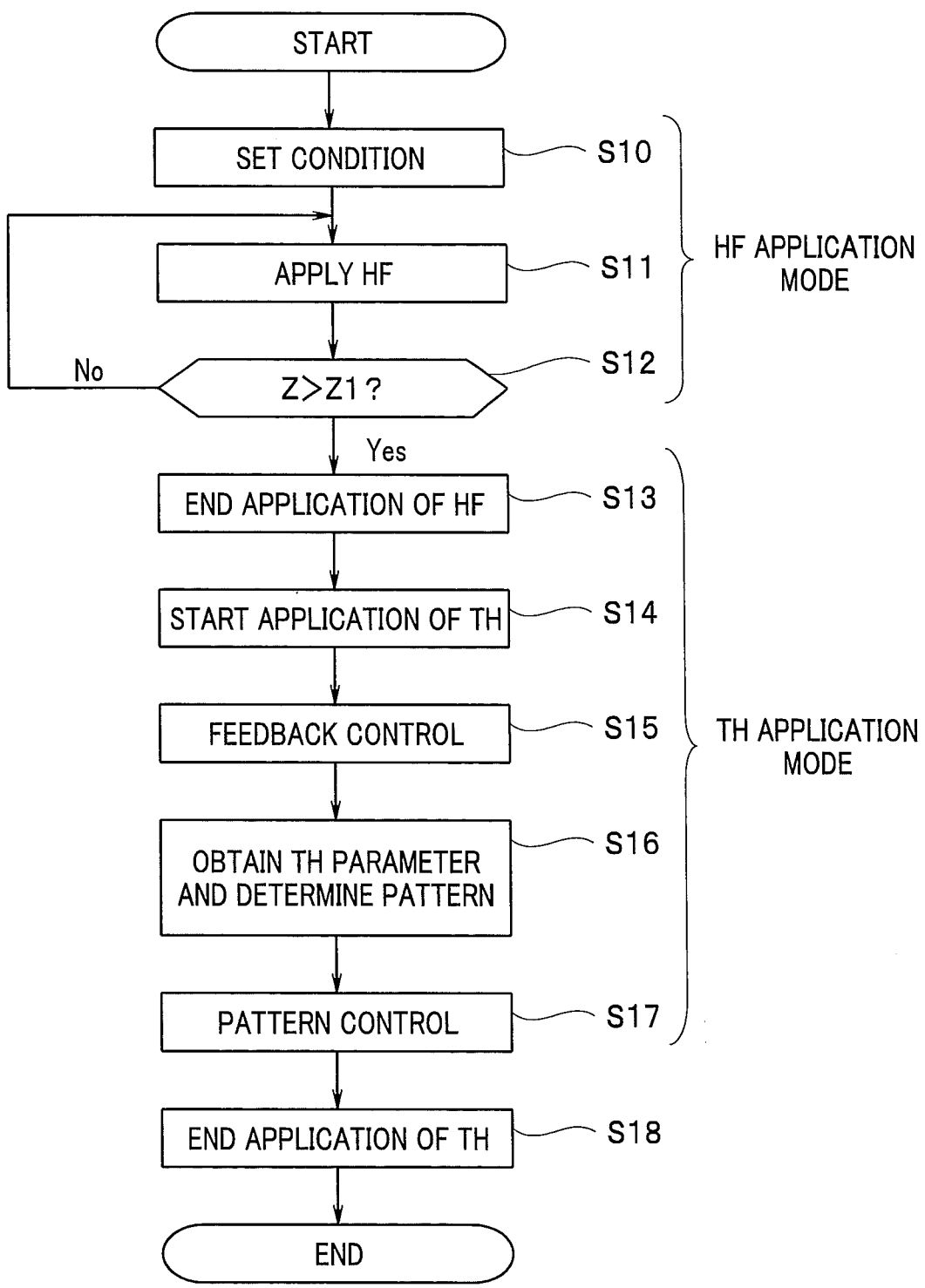
FIG. 5 is a flow chart for explaining a flow of processing of the treatment system according to the first embodiment.

A motion of the treatment system 10 will be described below with reference to a flow chart shown in FIG. 5.

<Step S10>

A surgeon inputs and sets treatment conditions to the control section 94 by using the operation panels 76 and 86. Examples of the treatment conditions include setting power Pset (W) for HF energy application mode, a setting temperature Tset (° C.) for thermal energy application mode, and a threshold value Z1 ($\Omega$) for an HF impedance Z for determining when to end HF energy application mode. Note that the treatment conditions will be described in detail later.

<Step S11>

The surgeon puts his or her fingers on the rings 33a and 33b of the handle portions 34a and 34b of the treatment instrument 11, operates the treatment instrument 11, and grasps a living tissue to be treated with the jaws 36a and 36b.

When the surgeon presses the pedal 13a of the foot switch 13 with a foot, application of HF energy to the living tissue between the electrodes 52a and 52b of the jaws 36a and 36b of the treatment instrument 11 starts. Note that the pedal 13a remains pressed during treatment. When the surgeon takes the foot off the pedal 13a, the power supply portion 12 forcibly stops outputting the energy.

HF outputted by the high-frequency power source 73 is controlled by constant power control to a predetermined setting power Pset (e.g., about 20 W to 150 W) set in step S10.

In HF energy application mode, Joule heat is generated to heat the living tissue itself. Dielectric breakdown, electric discharge, and the like arising from HF action destroy cell membranes in the living tissue. With the destruction of the cell membranes, released materials from the cell membranes are homogenized with extracellular components typified by collagen.

Figure 6:
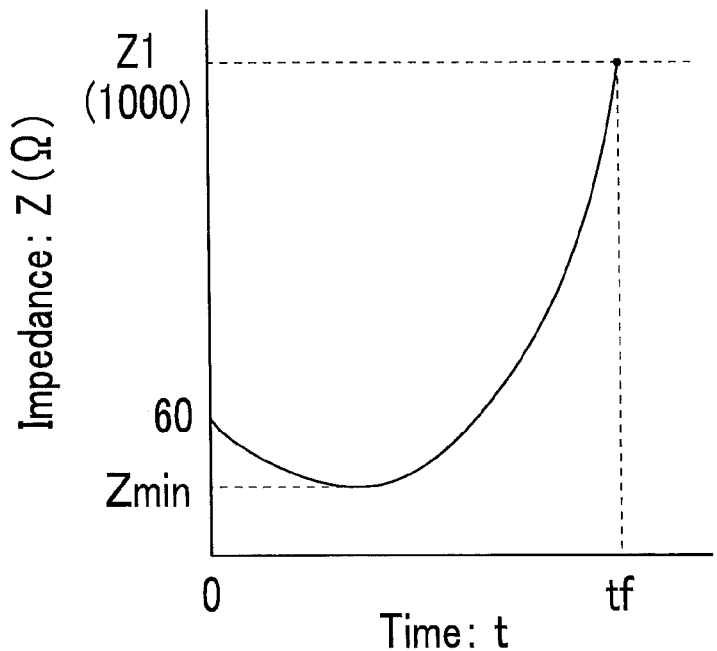
FIG. 6 is a graph showing change in impedance in high-frequency power application mode.

In HF energy application mode, the impedance Z for HF, i.e., the impedance Z in the grasped living tissue is calculated on the basis of HF information from the HF sensor 75. As shown in FIG. 6, the HF energy application under constant power control causes the impedance Z to be, for example, about 60$\Omega$ at the start of the HF energy application, decrease after the start to exhibit a minimum value Zmin, and increase after the exhibition.

<Step S12>

That is, since application of HF energy advances drying of the living tissue, the impedance Z for HF under constant power control rises. Completion of the process of destroying cell membranes in the grasped living tissue is sensed on the basis of the impedance Z. That is, since when the destruction process is completed, substances in cell membranes are released no longer, rise in the impedance Z accelerates. Additionally, when the impedance Z is high, appropriate HF energy application is difficult.

For the reason, the control section 94 (the HF control section 74) determines, on the basis of a predetermined threshold value Z1, whether to end HF energy application mode.

The threshold value Z1 is, for example, about 10$\Omega$ to 1500$\Omega$. Note that the surgeon need not set the threshold value Z1 if the threshold value Z1 is incorporated in advance in a program of the control section 94 (the HF control section 74). Alternatively, whether to end HF energy application mode may be determined by another method.

The HF control section 74 determines whether the impedance Z has exceeded the threshold value Z1 (e.g., 1000$\Omega$). If the HF control section 74 determines that a value of the impedance Z is less than the threshold value Z1 (NO in S12), the HF control section 74 continues applying HF energy.

<Step S13>

On the other hand, if the HF control section 74 determines that the impedance Z has exceeded the threshold value Z1 (YES in S12), the HF control section 74 controls the high-frequency power source 73 to stop outputting HF (t=tf in FIG. 6).

<Step S14>

If the HF control section 74 determines that the impedance Z has become not less than the threshold value Z1, a signal is transmitted from the HF control section 74 of the HF unit 72 to the TH control section 84 of the TH unit 82 via the communication line 91. Switching from HF energy application mode to TH energy application mode is performed.

<Step S15>

In an initial stage of TH energy application mode, the TH control section 84 supplies TH to the heater member 53 such that the temperature of the heater member 53 is a predetermined setting temperature Tset (e.g., about 120° C. to 300° C.). That is, the TH control section 84 performs constant temperature feedback control that increases/decreases TH output such that a temperature T of the heater member 53 is the temperature Tset set as the treatment condition in step S10.

The treatment in HF energy application mode has uniformed the living tissue and has raised thermal conductivity. For the reason, in TH energy application mode, heat from the heater member 53 is efficiently transferred to the living tissue. In TH energy application mode, proteins in the living tissue are integrally denatured, and removal of moisture that is a hindrance to hydrogen bonding between proteins is performed.

Figure 7:
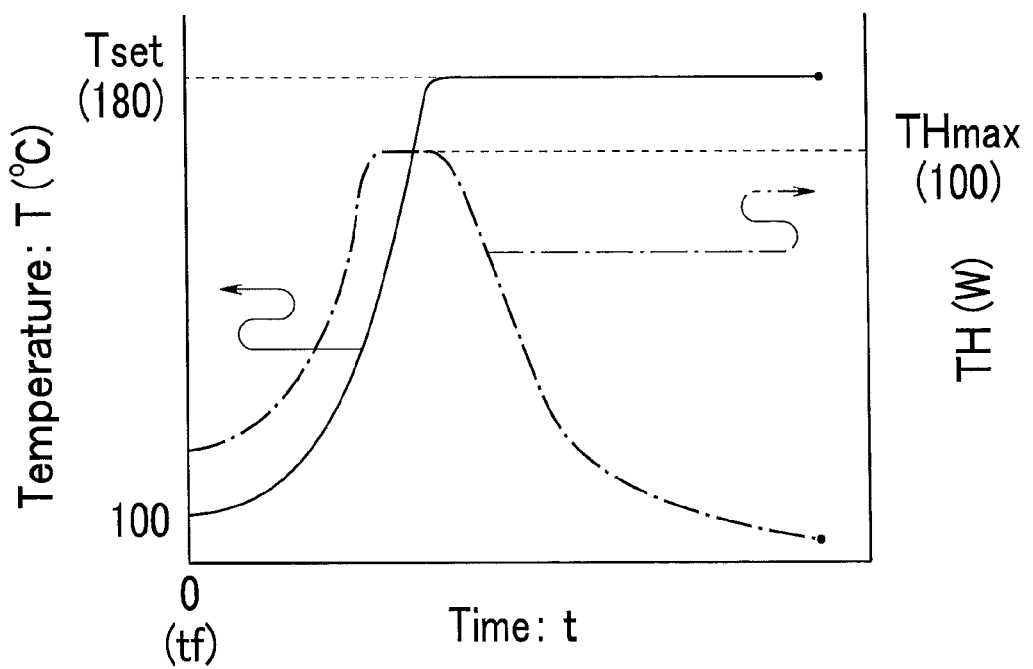
FIG. 7 is a graph showing change in temperature and change in power for heat generation in power-for-heat-generation application mode.

As shown in FIG. 7, the temperature T at a TH energy application mode start time is, for example, 100° C. Note that the TH energy application mode start time (t=0) shown in FIG. 7 is equivalent to a TF energy application mode end time (t=tf). Application of power for heat generation that is brought under constant temperature control aiming for the setting temperature Tset causes the temperature T of the heater member 53 to rise to the setting temperature Tset (e.g., 180° C.) and then be held at the setting temperature Tset.

In contrast, power TH for heat generation is high until the temperature rises to the setting temperature Tset. In other words, since temperature of the grasped living tissue having high thermal capacity needs to be raised in order to raise the temperature T of the heater member 53, the TH needs to be high.

Note that the TH exhibits a fixed value (THmax) from a time t1 to a time t2 in FIG. 7 because the value THmax is set to a maximum rated power (e.g., 100 W) of the power source 83 for heat generation. The value THmax is set to the maximum rated power because a power source having high maximum rated power is expensive and large. Note that the treatment system 10 does not matter much even when an inexpensive power source having low maximum rated power is used.

After the temperature T of the heater member 53 reaches the setting temperature Tset, the TH required to maintain the temperature becomes low. As the treatment advances further, and contraction or the like of the grasped living tissue advances, the TH becomes lower.

That is, after the temperature of the heater member 53 is raised to a predetermined temperature, the power (TH) for heat generation under constant temperature control for holding the temperature at the predetermined temperature increases after application of thermal energy starts and decreases after a maximum value is exhibited. The temperature of the heater member 53 is calculated from a resistance value of the heater member 53, i.e., current and voltage of the power (TH) for heat generation.

<Step S16>

Figure 8:
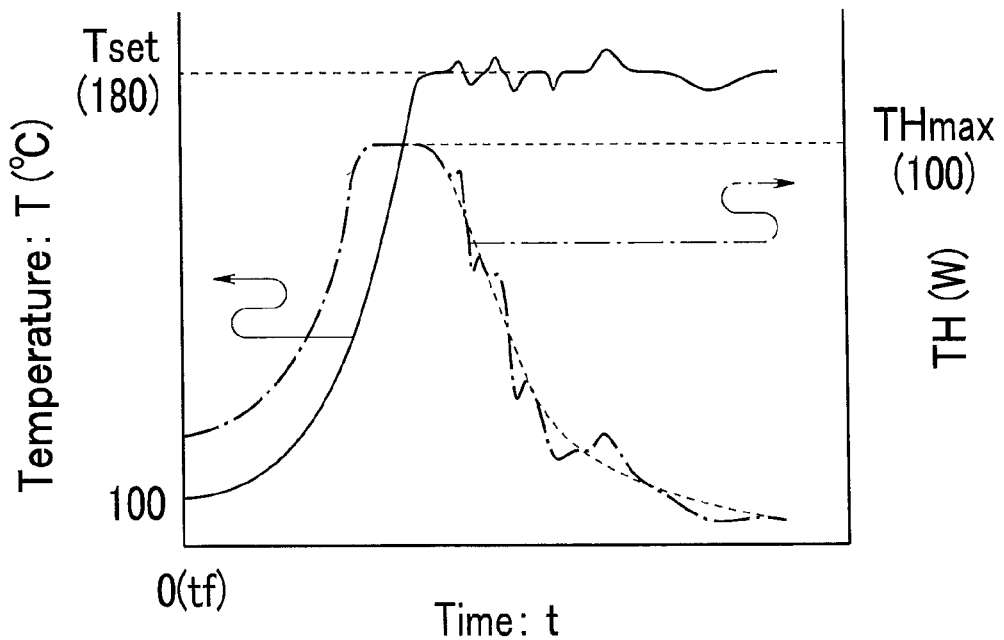
FIG. 8 is a graph showing change in temperature and change in power for heat generation in power-for-heat-generation application mode in the presence of disturbance.

Patterns shown in FIG. 7 of change in temperature and change in power in TH energy application mode are so-called ideal patterns. In actual treatment, as shown in FIG. 8, the temperature T of the heater member 53 may change due to disturbance. Disturbance here refers to a factor other than the living tissue being treated. That is, examples of disturbance include contact with a surrounding living tissue not being grasped, supply of moisture from an outside, and change in grasping force. The temperature T of the heater member 53 may change due to disturbance, regardless of progress of treatment of a living tissue.

When the temperature T increases or decreases due to disturbance, TH increases or decreases correspondingly in feedback control. In the case, unexpected thermal energy may be applied to a grasped living tissue. The application may make difficult the process of joining the living tissue through hydrogen bonding that requires fine energy application control. For the reason, a user needs to constantly monitor whether correct control is being performed, and operability may be poor.

Hydrogen bonding is a noncovalent attractive interaction which a hydrogen atom covalently bonded to a highly electronegative atom (an electronegative atom) forms with a lone pair of electrons such as on nitrogen, oxygen, sulfur, or fluorine or in a π-electron system that is located in a neighborhood. In proteins in a living tissue, a hydrogen bond is formed between an oxygen atom in a main chain and a hydrogen atom of an amide bond. Unlike simple joining through denaturation of proteins, moisture content control and temperature control at the time of joining are important for joining through hydrogen bonding. For the controls, precise control of thermal energy to be applied is important.

In the treatment system 10, when TH starts to decrease, the control section 94 (the TH control section 84) performs pattern control on the power source 83 for heat generation on the basis of a power decrease pattern for a case with no disturbance, i.e., in an ideal condition, in order to reliably perform the process of joining the living tissue through hydrogen bonding. That is, the control section 94 (the TH control section 84) changes a control method for the power source 83 for heat generation from feedback control to pattern control.

In order to perform pattern control, it is necessary to acquire the power decrease pattern in an ideal condition.

Figure 9:
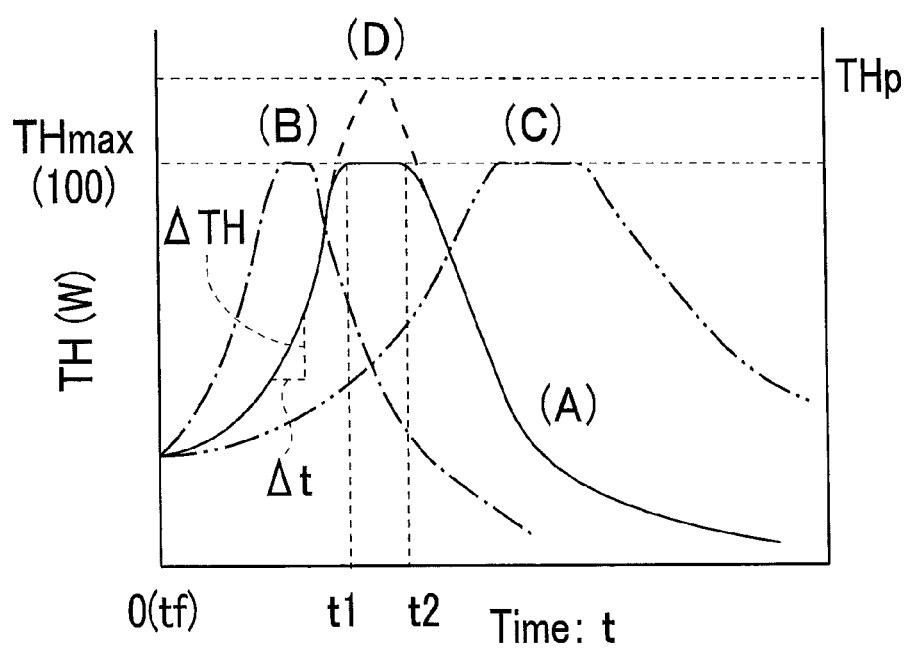
FIG. 9 is a graph showing change in power for heat generation in power-for-heat-generation application mode.

As shown in FIG. 9, ideal power decrease patterns (curves of decrease in TH with time) vary greatly according to the type and the like of a grasped living tissue. For example, curve (A) is for a tubular organ, such as a small intestine or a large intestine, curve (B) is for a blood vessel, and curve (C) is for a parenchyma organ, such as a lung, a liver, or a pancreas.

That is, in the case of a tissue having low thermal capacity, the temperature rises to the setting temperature Tset by brief application of thermal energy. After the rise, HW required to hold the temperature at the setting temperature Tset decreases rapidly. In contrast, in the case of a tissue having high thermal capacity, the temperature takes time to rise to the setting temperature Tset, and HW required to hold the temperature at the setting temperature Tset does not decrease rapidly.

It was found from pieces of experimental data which were acquired when various tissues were processed, that there is a correlation between a change state before TH decreases, i.e., an initial TH change pattern and a subsequent power decrease pattern when TH decreases.

The findings have enabled the control section 94 to predict a power decrease pattern indicating a subsequent change state (decrease pattern) of power for heat generation by using a parameter pth of power for heat generation which is based on an initial change state of power TH for heat generation.

For example, as shown by curves (A), (B), and (C) in FIG. 9, if TH reaches the value THmax set to the maximum rated power of the power source 83 for heat generation during feedback control, a time period (t1) for TH to reach the maximum value THmax or a time period (Δt=t2−t1) during which TH persists at the maximum value THmax and a power decrease pattern correspond well. The maximum value THmax is set to the maximum rated power. For the reason, a subsequent power decrease pattern can be predicted by using, as the parameter pth of power for heat generation, the time period (t1) for TH to reach the maximum value THmax or the time period Δt during which TH persists at the maximum value THmax.

As in curve (D) of FIG. 9, if TH exhibits a peak value THp during feedback control, a subsequent power decrease pattern could be predicted by using, as the parameter pth of power for heat generation, a time period for TH to reach the peak value THp as the maximum value THmax.

A subsequent power decrease pattern can also be predicted by using, as the parameter pth of power for heat generation, a rate of increase in TH (ΔTH/ΔT) (especially a maximum rate of increase) during increase in TH in an initial stage of feedback control.

A more precise power decrease pattern can, of course, be predicted by using, as the parameter pth of power for heat generation, two or more values selected from among the rate of increase in TH (ΔTH/ΔT), the maximum value THmax (the peak value THp), the time period (t1) for TH to reach the maximum value THmax, and the time period (t2−t1) during which TH persists at the maximum value THmax.

That is, a power decrease pattern when TH decreases can be predicted by using the parameter pth of power for heat generation that is made up of the rate of increase in TH (ΔTH/ΔT), the maximum value $TH_{max}$, the time period (t1) for TH to reach the maximum value THmax, or the time period Δt during which TH persists at the maximum value THmax.

Note that a power decrease pattern can be expressed as a table indicating a correspondence between time (t) and TH or a calculation formula in the form of TH=f(t). TH is calculated by substituting time (t) into the calculation formula TH=f(t).

If a power decrease pattern is expressed in table form, tables for a plurality of power decrease patterns are prepared. One table is selected on the basis of the parameter pth of power for heat generation.

If a power decrease pattern is expressed as a calculation formula, a curve of change in HT with time, TH=f(t) is derived by substituting a value of the parameter pth of power for heat generation into the derivation formula TH=f(pth,t).

In the treatment system 10, various power decrease patterns which are calculated in advance on the basis of pieces of experimental data are stored as tables or a calculation formula in the memory 92.

For the reason, the control section 94 can acquire a power decrease pattern used for control from the tables or the calculation formula stored in the memory 92 by using the parameter pth of power for heat generation based on a change state of TH during feedback control.

Note that, in the case of the power supply portion 12, to which a plurality of different treatment instruments can be connected, a set of a plurality of power decrease patterns corresponding to the respective treatment instruments can be stored in the memory 92 such that one of the power decrease patterns can be selected according to the connected treatment instrument.

<Step S17>

The control section 94 (the TH control section 84) having determined (acquired) a power decrease pattern changes the control method for the power source 83 for heat generation from constant temperature control based on the temperature T of the heater member 53 to pattern control that controls a power value according to the power decrease pattern.

<Step S18>

Thermal energy is applied to the living tissue according to the power decrease pattern until the application of TH ends.

In the treatment system 10, there is no possibility that unintentional thermal energy may be applied to a living tissue due to, e.g., disturbance, and the operability is good.

The treatment system 10 and the actuation method for the treatment system 10 easily implements a process of removing moisture from a living tissue through application of thermal energy and joining the living tissue through hydrogen bonding.

Second Embodiment

A treatment system 10B according to a second embodiment will be described. Since the treatment system 10B is similar to the treatment system 10, constituent elements having identical functions are denoted by identical reference numerals, and a description of the constituent elements will be omitted.

Figure 10:
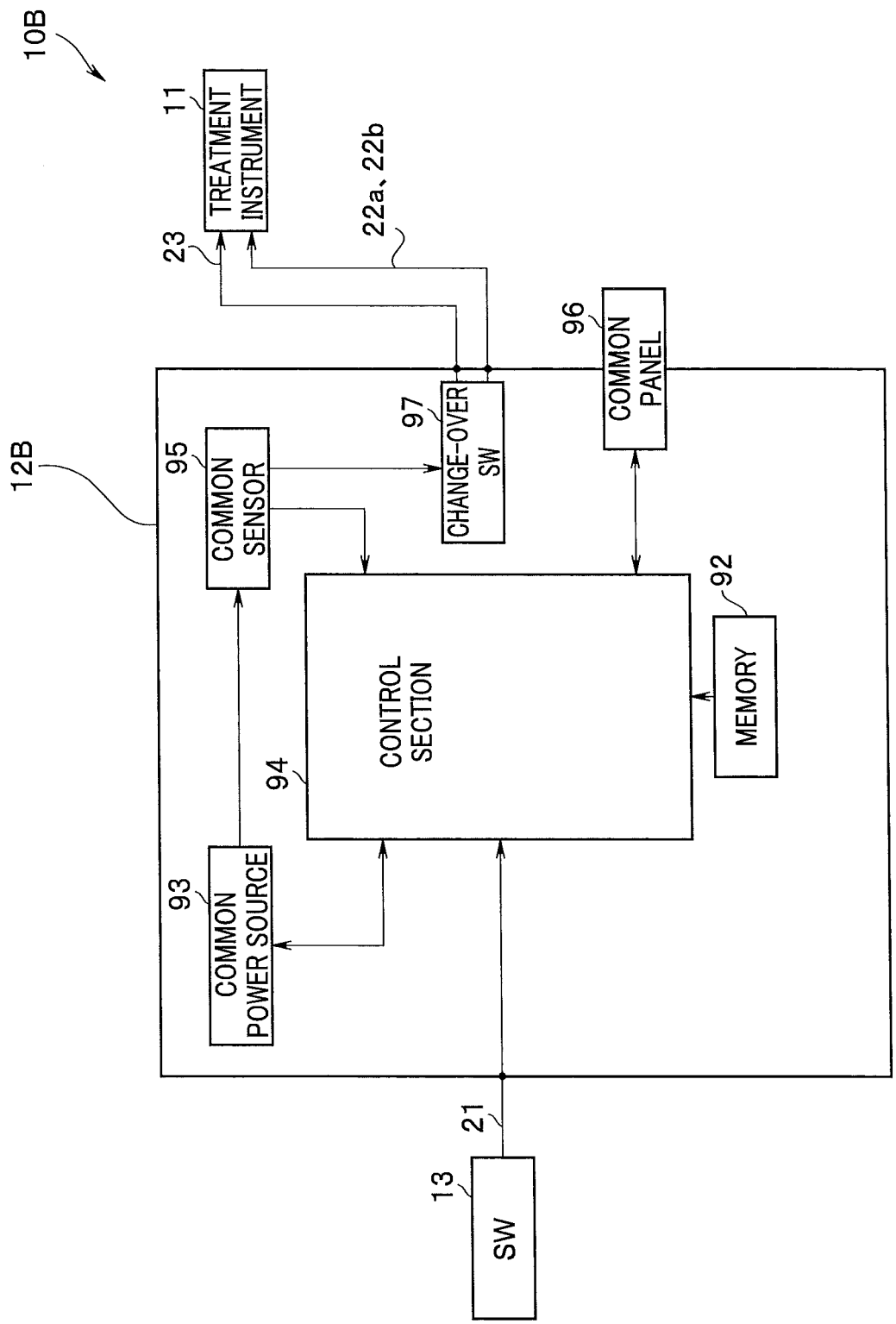
FIG. 10 is a configuration diagram of a treatment system according to a second embodiment.

As shown in FIG. 10, a power supply portion 12B of the treatment system 10B has a common power source 93 which has a high-frequency power source function and a power-source-for-heat-generation function and a change-over switch 97 which switches an output destination. The power supply portion 12B further has a common sensor 95 which has the function of an HF sensor 75 and the function of a TH sensor 85.

As already described, the high-frequency power source 73 and the power source 83 for heat generation do not simultaneously output power even in the treatment system 10 according to the embodiment. For the reason, in the treatment system 10B, the one common power source 93 functions as a high-frequency power source or a power source for heat generation under control of a control section 94.

That is, in HF application mode, HF outputted by the common power source 93 is sent to HF lines 22a and 22b via the change-over switch 97. In TH application mode, TH outputted by the common power source 93 is sent to the TH line 23 via the change-over switch 97.

Note that the common sensor 95 functions as an HF sensor or a TH sensor and that a common panel 96 functions as an HF panel or a TH panel.

The treatment system 10B and an actuation method for the treatment system 10B have the same effects as effects of the treatment system 10 and the like and are simple in configuration.

Note that, in a treatment system in which respective heater members are disposed at jaws 36a and 36b of a treatment instrument 11, respective power sources for heat generation may be controlled on the basis of temperatures of the heater members. Alternatively, control may be performed by one power source for heat generation on the basis of an average temperature of the two heater members.

As described above, a control method for a treatment system according to the embodiment includes a step of setting a treatment condition for a treatment system including one pair of grasping members which apply high-frequency power energy and thermal energy to a grasped living tissue, a high-frequency power source which outputs high-frequency power for applying the high-frequency power energy, and a power source for heat generation which outputs power for heat generation for applying the thermal energy, a step of controlling the high-frequency power source on the basis of the treatment condition and applying the high-frequency power energy to the living tissue, a step of starting application of the thermal energy under constant temperature control on the basis of the treatment condition after the application of the high-frequency power energy ends, a step of acquiring a parameter of power for heat generation on the basis of an initial change state of the power for heat generation that increases after the start of the application of the thermal energy and decreases after exhibiting a maximum value under the constant temperature control, a step of acquiring a power decrease pattern which predicts a subsequent change state of the power for heat generation by using the parameter of power for heat generation, and a step of performing pattern control on the power for heat generation on the basis of the power decrease pattern.

The present invention is not limited to the above-described embodiments and the like. Various changes, modifications, and the like can be made without departing from the scope of the present invention.

What is claimed is:

1. A treatment system comprising:
a power source for heat generation which outputs power for heat generation;
a grasping member having a heating element which applies the power for heat generation as thermal energy to a living tissue;
a storage section storing a plurality of power decrease patterns corresponding to a plurality of types of living tissues to be treated, each of which is a prediction about a change state of the power for heat generation; and
a control section which acquires one power decrease pattern from the storage section on the basis of a parameter of power for heat generation which is based on a change state of the power for heat generation outputted by the power source for heat generation that is subjected to constant temperature control, and changes a control method for the power source for heat generation from feedback control to hold a temperature of the heating element at a predetermined temperature to pattern control based on the power decrease pattern after the one power decrease pattern is acquired.

2. The treatment system according to claim 1, further comprising
a high-frequency power source which outputs high-frequency power, wherein
the grasping member has electrodes which apply the high-frequency power as high-frequency power energy to the living tissue, and
the control section applies the thermal energy after application of the high-frequency power energy ends.

3. The treatment system according to claim 2, wherein the high-frequency power source and the power source for heat generation are made up of a common power source.

4. The treatment system according to claim 2, wherein the control section ends application of the high-frequency power energy and applies the thermal energy when the control section senses completion of a process of destroying a cell membrane in the living tissue on the basis of a change in impedance of the high-frequency power, moisture is removed from the living tissue, and the living tissue is joined through hydrogen bonding.

5. The treatment system according to claim 1, wherein the parameter of power for heat generation comprises at least one of a rate of increase in the power for heat generation, a maximum value of the power for heat generation, a time period for the power for heat generation to reach the maximum value, and a time period during which the power for heat generation persists at the maximum value.

6. The treatment system according to claim 5, wherein the maximum value of the power for heat generation is set to maximum rated power of the power source for heat generation, and the parameter of power for heat generation is the time period during which the power for heat generation persists at the maximum value.

7. The treatment system according to claim 1, wherein the storage section stores the power decrease pattern used for the pattern control as a table or a calculation formula which is based on experimental data.

8. The treatment system according to claim 1, wherein the control section performs the constant temperature control on the power source for heat generation on the basis of temperature which is calculated from a resistance value of the heating member that is made of a material having a positive temperature coefficient of resistance.

9. An actuation method for a treatment system, comprising:
a step in which power for heat generation outputted by a power source for heat generation that is subjected to feedback control to hold a temperature of the heating element of a grasping member at a predetermined temperature by a control section is released as thermal energy by the heating element of a grasping member;
a step of acquiring, by the control section, a parameter of power for heat generation on the basis of a change state of the power for heat generation;
a step of acquiring, by the control section, one power decrease pattern from a plurality of power decrease patterns corresponding to types of living tissue to be treated, the one power decrease pattern being a prediction about a subsequent change state of the power for heat generation from a storage section by using the parameter of power for heat generation; and
a step of changing, by the control section, a control method for the power source for heat generation from the feedback control to pattern control based on the one power decrease pattern.

10. The actuation method for the treatment system according to claim 9, further comprising a step in which high-frequency power outputted by a high-frequency power source that is controlled by the control section is released as high-frequency power energy by electrodes of the grasping member before a thermal energy releasing step.

11. The actuation method for the treatment system according to claim 10, wherein the high-frequency power source and the power source for heat generation are made up of a common power source.

12. The actuation method for the treatment system according to claim 9, wherein the parameter of power for heat generation comprises at least one of a rate of increase in the power for heat generation, a maximum value of the power for heat generation, a time period for the power for heat generation to reach the maximum value, and a time period during which the power for heat generation persists at the maximum value.

13. The actuation method for the treatment system according to claim 12, wherein the maximum value of the power for heat generation is set to maximum rated power of the power source for heat generation, and the parameter of power for heat generation is the time period during which the power for heat generation persists at the maximum value.

14. The actuation method for the treatment system according to claim 9, further comprising a step of storing in advance, by the storage section, a table or a calculation formula which is based on experimental data for acquiring the power decrease pattern used for control from the parameter of power for heat generation.

15. A treatment system comprising:
a high-frequency power source which outputs high-frequency power;

a power source for heat generation which outputs power for heat generation;

a grasping member having electrodes that apply the high-frequency power as high-frequency power energy to a living tissue, and a heating element which applies the power for heat generation as thermal energy to the living tissue after application of the high-frequency power energy ends;

a storage section storing a plurality of power decrease patterns corresponding to a plurality of types of living tissues to be treated, each of which is a prediction about change state of the power for heat generation; and a control section which acquires one power decrease pattern from the storage section on the basis of a parameter of power for heat generation which is based on a change state of the power for heat generation outputted by the power source for heat generation that is subjected to constant temperature control, and changes a control method for the power source for heat generation from feedback control to hold a temperature of the heating element at a predetermined temperature to pattern control based on the power decrease pattern after the one power decrease pattern is acquired.

16. An actuation method for a treatment system, comprising:

a step of grasping a living tissue with a grasping member having electrodes to apply a high-frequency power outputted by a power source for high-frequency power as high-frequency power energy to the living tissue;

subsequent to the application of the high-frequency power energy to the living tissue, a step in which power for heat generation outputted by a power source for heat generation that is subjected to feedback control to hold a temperature of a heating element of the grasping member at a predetermined temperature by a control section is released as thermal energy by the heating element of the grasping member;

a step of acquiring, by the control section, a parameter of power for heat generation on the basis of a change state of the power for heat generation;

a step of acquiring, by the control section, one power decrease pattern from a plurality of power decrease patterns corresponding to types of living tissue to be treated, the one power decrease pattern being a prediction about a subsequent change state of the power for heat generation from a storage section by using the parameter of power for heat generation; and a step of changing, by the control section, a control method for the power source for heat generation from the feedback control to pattern control based on the one power decrease pattern.

* * * * *